United States Patent [19]
Kitamura et al.

[11] Patent Number: 4,962,240
[45] Date of Patent: Oct. 9, 1990

[54] METHOD FOR SYMMETRICALLY DIMERIZING PHENOLS AND PROCESS FOR PRODUCING BIPHENOLS

[75] Inventors: Taku Kitamura; Noriko Kurokawa, both of Ichikawa; Katsuji Takahashi, Chiba, all of Japan

[73] Assignee: Danippon Ink and Chemicals, Inc., Tokyo, Japan

[21] Appl. No.: 321,067

[22] Filed: Mar. 9, 1989

[30] Foreign Application Priority Data

Mar. 11, 1988 [JP] Japan ................................. 63-56013
Jun. 24, 1988 [JP] Japan ................................ 63-154651

[51] Int. Cl.$^5$ ..................... C07C 39/14; C07C 37/11
[52] U.S. Cl. .................................. 568/730; 568/722; 568/727; 568/729
[58] Field of Search ................ 568/730, 722, 727, 729

[56] References Cited

U.S. PATENT DOCUMENTS 4,195,189 3/1980 Earley ................................. 568/730

FOREIGN PATENT DOCUMENTS 55-120529 9/1980 Japan ................................. 568/730
58-140034 8/1983 Japan ................................. 568/730
61-200935 9/1986 Japan ................................. 568/730
62-077341 4/1987 Japan ................................. 568/730

Primary Examiner—Werren B. Lone
Attorney, Agent, or Firm—Sherman and Shalloway

[57] ABSTRACT

A method for symmetrically dimerizing phenols which comprises oxidizing phenols in molten state in the liquid phase using a transition metal compound as a catalyst and an oxygen-containing gas as an oxidizing agent to conduct dimerization; and a process for producing diphenols which comprises oxidizing phenols in molten state in the liquid phase using a transition metal compound as a catalyst and an oxygen-containing gas as an oxidizing agent to conduct dimerization, and then interrupting introduction of the oxygen-containing gas to conduct a proton disproportionation reaction.

20 Claims, No Drawings

METHOD FOR SYMMETRICALLY DIMERIZING PHENOLS AND PROCESS FOR PRODUCING BIPHENOLS

This invention relates to a method for symmetrically dimerizing phenols. More specifically, this invention relates to a method for symmetrically dimerizing phenols by an oxidative coupling reaction and a process for producing biphenols.

It is known that by an oxidative coupling reaction, phenols are formed into symmetrically dimerized products, i.e. biphenols and/or diphenoquinones or asymmetrically dimerized products, i.e. phenoxyphenols, and/or oligomerized polyphenylene ethers. Among these compounds, the symmetrically dimerized products, above all, diphenols have lately attracted attention as anti-oxidants, starting materials of polyesters, polycarbonates or epoxy resins, or intermediates of dyestuffs and medicaments However, when they are used as starting materials of polyesters, polycarbonates or epoxy resins, it is important to suppress a side reaction, i.e. formation of asymmetrically dimerized products hard to separate and remove, such as phenoxyphenols, etc. as much as possible.

Many examples of studies have been known about the symmetrical dimerization reaction of phenols, especially, 2,6-dialkylated phenols. For instance, Japanese Laid-open Patent Application No. 120529/1980 (corresponding to U S. Pat. No. 4,195,189) discloses a method using an activated copper salt as an oxidizing agent. However, this method requires a large amount of the copper salt and is thus economically disadvantageous. Further it necessitates a treatment of a heavy metal (copper) after the reaction, and the procedure is therefore complex.

To remedy these defects, a method using air or oxygen as an oxidizing agent has been proposed. For example, Japanese Laid-open Patent Application No. 200935/1986 describes a method in which the oxidative dimerization of 2,6-di-t-butylphenol is carried out using oxygen as an oxidizing agent and potassium hydroxide as a catalyst. This method is free from the defects associated with the method using the metallic compound as an oxidizing agent, but a ratio (hereinafter referred to as a "reaction selectivity") at which to convert consumed 2,6-di-t-butylphenol into a symmetrically dimerized product is as low as 75.6% and unsatisfactory. This holds true of a method described in Japanese Laid-open Patent Application No. 77341/1987 wherein a transition metal salt is used as a catalyst and oxygen as an oxidizing agent. It has been reported that when 2,6-xylenol is used as a starting material, a yield of tetramethyldiphenol is low, and by-products hard to separate and remove, such as phenoxyphenol, etc. are formed in large amounts.

When the transition metal compound is used as a catalyst, biphenols formed in the system are overoxidized into diphenoquinones by oxygen, etc. present in the system. The diphenoquinones formed here can be converted into biphenols by a proton disproportionation reaction with unreacted starting phenols or by a hydrogenation reaction in the presence of a catalyst which is described in Japanese Laid-open Patent Application No. 140034/1983.

Nevertheless, the former method has a defect that if the disproportionation is conducted with the transition metal compound left in the system, the reaction rate is low or the disproportionation cannot be completed enough. The latter method is economically disadvantageous because it requires another step.

Thus, a method for dimerizing phenols by oxidation (i.e. a method for oxidative dimerization of phenols) that meets all the selectivity, yield and economics has not yet been known.

It is an object of this invention to improve the aforesaid method for symmetrically dimerizing the phenols by oxidation.

The present inventors have made extensive studies to achieve this object, and consequently found that when phenols in molten state are oxidized in the liquid phase preferably in the substantial absence of a solvent by introducing an oxygen-containing gas, a selectivity of a dimerization reaction is high, and byproducts hard to separate and remove, such as phenoxyphenol, etc. are not formed, that when the introduction of the oxygen-containing gas into the reaction system is interrupted and the reaction system is preferably heated at a temperature higher than the temperature of the oxidative dimerization to advance the thermal proton disproportionation between diphenoquinones secondarily formed in the reaction system and phenols are easily converted into biphenols, and that when part or the whole of the transition metal compound as a catalyst is deactivated, the proton disproportionation reaction can efficiently proceed.

Thus, this invention provides a method for symmetrically dimerizing phenols which comprises oxidizing phenols in molten state in the liquid phase using a transition metal compound as a catalyst and an oxygen-containing gas as an oxidizing agent to conduct dimerization, and a process for producing biphenols which comprises oxidizing phenols in molten state in the liquid phase using a transition metal compound as a catalyst and an oxygen-containing gas as an oxidizing agent to conduct dimerization, and then interrupting introduction of the oxygen-containing gas to conduct a proton disproportionation reaction.

The products obtained by symmetrical dimerization are biphenols, diphenoquinones and mixtures thereof. The proportions of biphenols and diphenoquinones formed can vary depending on selection of the catalyst used and the reaction conditions. It is possible that biphenols and diphenoquinones can readily be converted into each other by the redox reaction. Accordingly, the proportions of these two compounds are not industrially important. The method in this invention ca advantageously be used whether the final product is biphenols or diphenoquinones. The phenols used in this invention as starting material are not particularly limited. For example, phenols represented by formula (I)

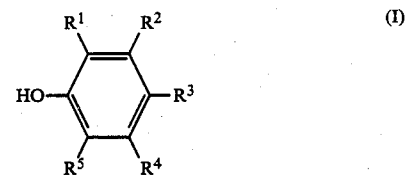

wherein $R^1$, $R^2$, $R^3$, $R^4$ and $R^5$ may be the same or different and each denotes a hydrogen atom, a hydrocarbon group having 1 to 8 carbon atoms, an alkoxy group or an allyloxy group, or the adjacent R groups may form a cyclic structure by a suitable bonding group such as a polymethylene group or a dioxymethylene group, provided at least one of the substituents in the ortho- or para-position that directly participate in dimerization, i.e. $R^1$, $R^3$ and $R^5$ has to be a hydrogen atom.

Examples of the phenols are phenol, o-cresol, o-ethylphenol, o-isopropylphenol, o-t-butylphenol, o-cyclohexylphenol, guaiacol, o-allylphenol, o-benzylphenol, o-phenoxyphenol, p-cresol, p-ethylphenol, p-iso-propylphenol, p-t-butylphenol, p-cyclohexylphenol, p-methoxyphenol, p-allylphenol, p-benzylphenol, p-phenoxyphenol, 2,6-xylenol, 2,6-diisopropylphenol, 2,6-di-t-butylphenol, 2-methyl-6-t-butylphenol, 2-ethyl-6-methylphenol, 2-methoxy-6-methylphenol, 2,6-diphenylphenol, 2,6-dicyclohexylphenol, 2,4-dimethylphenol, 2,4-di-t-butylphenol, 2-ethyl-4-methylphenol, 2-methoxy4-methylphenol, 4-methoxy-2-methylphenol, 2,4-dicyclohexylphenol, 2,3,6-trimethylphenol, 2,3,4-trimethylphenol, 2,3,4,5-tetramethylphenol and 3,5-xylenol.

Of these phenols, 2,6-xylenol, 2,3,6-trimethylphenol, 2,6-di-t-butylphenol, o-cresol and 2,4-xylenol are most preferable.

In the oxidative coupling reaction of phenols, transition metal compounds are used as a catalyst. The catalyst used in this reaction is various transition metal ions according to types of the phenols. Examples thereof are copper (II), iron (II), iron (III), lead (II), vanadium (V), vanadyl [VO(III)], cobalt (II), manganese (II), manganese (III), molybdenum (V), tungsten (V), palladium (II) and palladium (IV). Of these, copper, lead, iron, vanadium, cobalt and manganese are especially preferable. The amount of the transition metal compound varies with the type of the metal ion. It is usually 0.001 to 2.0 mol %, preferably 0.01 to 1.0 mol % per mol of phenols. A combination of the transition metal compounds is also available.

The metal ions subjected to the reaction are commonly used in the form of inorganic salts (e.g. a chloride, a sulfate and a nitrate), organic salts (e.g. an acetate and an oxalate) or metallic soaps (e.g. a naphthenate, an octylate and a stearate). The metallic soaps may be those diluted with a solvent such as toluene, mineral terpene or kerosene. It is however preferable that they are volatilized by raising the temperature and the reaction system is kept in the substantial absence of a solvent. Moreover, these metallic ions can also be used in the form of metal complexes using as ligands cyclic multidentate ligands such as phthalocyanines and porphyrins, glyoximates such as dimethyl glyoximate and multidentate Schiff base compounds such a bissalicylidene ethylene diiminate and bissalicylidene trimethylene diiminate. They are used by being dissolved or dispersed in phenols.

One of the characteristic features of this invention is that the oxidative dimerization reaction can be performed by directly introducing an oxygen-containing gas to molten phenols.

Further, as will be later described, it is also possible in this invention to continuously conduct in one and the same reactor two steps under different atmospheres and different reaction temperatures, i.e. a step of an oxidative dimerization reaction and a step of a proton disproportionation between diphenoquinones and phenols (hereinafter referred to as a "first step" and a "second step" respectively). For the reactions to efficiently proceed it is especially required to meet predetermined temperature conditions. To meet the temperature conditions, the reaction in the absence of a solvent that does not undergo limitation of the reaction temperature (boiling point) is most advantageous. The first step is an oxidative dimerization step which comprises oxidizing molten phenols using a transition metal compound as a catalyst and oxygen as an oxidizing agent to conduct dimerization. The second step is a step of interrupting introduction of an oxygen-containing gas to conduct proton disproportionation preferably in a inert atmosphere of nitrogen, etc.

Namely, the first step is performed by blowing an oxygen-containing gas, e.g. oxygen or oxygen diluted with an inert gas into phenols melted in the reactor. The amount of oxygen introduced into the system is not particularly limited, but the range of from 1 ml/min to 500 ml/min per mol of phenols is operationally preferable. In case of oxygen diluted with the inert gas, the total amount of the gas being introduced may be increased by an amount corresponding to the above oxygen amount according to the rate of dilution. For example, when a dry air is used, the gas may be introduced in the range of from 5 ml/min to 2500 ml/min. The introduction of oxygen can be performed not only under normal pressure but also under increased pressure. On this occasion, it is advisable to supplement oxygen consumed in the vessel and immediately remove water formed by the reaction outside the system.

Biphenols and also diphenoquinones are formed as dimerized products; their proportions vary with the type or the amount of the metal catalyst.

However, when the biphenols are obtained in accordance with this invention, the proportions of the biphenols and the diphenoquinones formed at this stage are substantially not important. This is because when heating is conducted without the contact with oxygen and preferably with the aid of a catalyst deactivator on condition that the starting phenols, the biphenols and the diphenoquinones are mixed at a suitable composition ratio, proton disproportionation proceeds between two molecules of the starting phenols and one molecule of the diphenoquinones and the biphenols alone are finally afforded as dimerized products independent of the composition ratio of the biphenols and the diphenoquinones before disproportionation.

A temperature of the oxidation reaction varies with a melting point and boiling point of the molten phenols. It is usually 130° to 220° C, preferably 160° to 200° C. It is advisable that the starting material and the reaction product are always kept in molten state during the reaction.

In the second step, the introduction of the oxygen-containing gas as an oxidizing agent is interrupted to conduct the thermal disproportionation reaction preferably while gradualy introducing a non-oxidizing gas such as a nitrogen gas and without removing the transition metal compound used in the first step. At this time, the reaction is effected at a temperature higher than the temperature of the oxidation, preferably a temperature of about 10° to 30° C higher than the temperature of the oxidation.

In the disproportionation reaction step, protons can only thermally be disproportionated. However, when the transition metal compound is used in the large amount in the first step, the proton disproportionation is sometimes hindered. For example, the diphenoquinones are not converted into biphenols at a sufficient ratio or the convertion takes a considerable time. In this case, it is advisale that for deactivating part or the whole of the transition metal compound catalyst used in the first step and remaining in the reactor, a deactivator of the transition metal compound catalyst is added in an amount of 0.001 to 0.1 mol per mol of the phenols after the oxidation reaction but before the proton disproportionation.

Examples of the deactivator are compounds having a coordinating ability to transition metal ions and containing a nitrogen, oxygen, sulfur or phosphorus atom as a ligand atom, such as aminoalcohols, polyamines, polyaminopolyethers, aminothiols, phosphines and aminocarboxylic acids. Concrete examples are ethanolamine, diethanolamine, triethanolamine, alaninol, aminophenol, ethylenediamine, diethylenetriamine, polyethyleneimine, hexamethylenediamine, phenylenediamine, trimethylenediamine, bipyridine, phenanthroline, aminated polyethylene glycol, cysteamine, aminothiophenol, triphenylphosphine, glycine, beta-alanine, aminobenzoic acid, iminodiacetic acid and dithiocarbamic acid ester. Of these, diethanolamine, diethylenetriamine, cysteamine and aminophenol are preferable.

The formed diphenols are usually isolated by crystallization and filtration from a solvent such as toluene, xylene, acetone, methyl isobutyl ketone, methanol or butanol. Since the proportions of the biphenols and the diphenoquinones have a great influence on a purity and a yield of the final biphenols, it is an important technical problem in producing the biphenols that the proton disproportionation reaction proceeds advantageously.

As has been stated in detail above, the method in this invention can easily dimerize the molten phenols by oxidation with oxygen using the transition metal compound as a catalyst and easily afford the corresponding biphenols.

The following Examples and Comparative Example illustrate this invention in more detail. In said Examples, percentages are on the weight basis.

EXAMPLE 1

To 103.0 g of 2,6-di-t-butylphenol in a 200-milliliter flask fitted with a reflux condenser and a stirrer was added 1.6 g of manganese naphthenate (8% mineral terpene solution). While elevating the temperature to 170° C, terpene was volatilized, and a dry air was then introduced under normal pressure at a rate of 140 ml./min. Eight hours after starting the reaction, the content was sampled and analyzed by gas chromatography using p-cumylphenol as a inner standard. The composition of the reaction mixture and the reaction selectivity are as follows.

| | |
|---|---|
| 3,3',5,5'-tetra-t-butyl-4,4'-dihydroxydiphenyl | 20.6% |
| 3,3',5,5'-tetra-t-butyl-4,4'-diphenoquinone | 10.5% |
| 2,6-di-t-butylphenol | 68.1% |
| asymmetrically dimerized products[*1] | 0.0% |
| others | 0.8% |
| reaction selectivity[*2] | 97.5% |

NOTES:
[*1] The asymmetrically dimerized products means 4-(2,6-di-t-butylphenoxy)-2,6-di-t-butylphenol, etc.
[*2] A ratio (%) at which to convert 2,6-di-t-butylphenol consumed into a symmetrically dimerized product. For example, in the above case, it is $$\frac{20.6 + 10.5}{20.6 + 10.5 + 0.0 + 0.8} \times 100 = 97.5\ (\%)$$

EXAMPLES 2 to 8

The reaction was performed in the same way as in Example 1 except that the phenols and the metallic soaps as a catalyst were changed as shown in Table 1. Eight hours later (twenty hours later in Example 3), the composition of the reaction liquid was analyzed. The results are shown in Table 1.

TABLE 1

| | | Catalyst | | Reaction selectivity | | | | | Reaction selectivity |
|---|---|---|---|---|---|---|---|---|---|
| Example No. | Phenols | Type | Amount | Phenols | Biphenols | Diphenoquinons | Asymmetrically-dimerized products | Others | |
| 2 | 2,6-Xylenol | Cobalt naphtenate (5% solution of mineral terpene) | 1.4 g | 89.5% | 6.8% | 3.6% | 0.0% | 0.1% | 99.0% |
| 3 | 2,6-Xylenol | Cobalt naphtenate (5% solution of mineral terpene) | " | 40.1% | 16.3% | 43.4% | 0.0% | 0.2% | 99.7% |
| 4 | 2,6-DTBP[*3] | Manganese napthenate (6% solution of xylene) Cobalt naphtenate (6% solution of xylene) | 0.8 g 0.7 g | 60.9% | 29.0% | 8.6% | 0.0% | 1.5% | 96.2% |
| 5 | 2,6-Xylenol | Copper oleate (5% solution of mineral terpene) | 3.0 g | 72.5% | 21.3% | 4.5% | 0.0% | 1.7% | 93.8% |
| 6 | 2,6-DTBP[*3] | Iron naphtenate (5% solution of mineral terpene) | 1.7 g | 67.2% | 22.0% | 10.0% | 0.0% | 0.8% | 97.6% |
| 7 | 2,6-DTBP[*3] | Lead naphthenate (30% solution of mineral terpene) | 1.3 g | 65.4% | 15.6% | 18.3% | 0.0% | 0.8% | 97.7% |
| 8 | 2,6-DTBP[*3] | Naphthenate salt of rare earth metal[*4] (4% solution of mineral terpene) | 5.2 g | 77.8% | 7.5% | 13.5% | 0.0% | 1.2% | 94.6% |

NOTES:
[*3] 2,6-di-t-butylphenol
[*4] mixture composed mainly of cerium (Ce) and containing some other rare earth metals

COMPARATIVE EXAMPLE 1

The reaction was performed in the same way as described in Example 1 of Japanese Laid-open Patent Application No. 77341/1987 except using 300 g of 2,6-di-t-butylphenol instead of 200 g of 2,6-xylenol.

That is, 5 g of manganous acetate tetrahydrate [Mn(CH$_3$COO)$_2$.4H$_2$O], 300 g of 2,6-di-t-butylphenol and 500 g of N,N-dimethylformamide were charged in a flask and heated to 150° C. Subsequently, a dry air was introduced at a rate of 1.5 liters/min. Six hours and ten hours after starting the reaction, the content was sampled, and the composition of the reaction liquid was analyzed. The results are as follows.

|  | After 6 hrs | After 10 hrs |
|---|---|---|
| 3,3',5,5'-tetra-t-butyl-4,4'-dihydroxydiphenyl | 8.2% | 53.1% |
| 3,3',5,5'-tetra-t-butyl-4,4'-diphenoquinone | 20.1% | 7.2% |
| asymmetrically dimerized products | 1.0% | 2.9% |
| 2,6-di-t-butylphenol | 66.8% | 30.6% |
| Others | 3.9 | 6.2% |

EXAMPLE 9

To 103 g of 2,6-di-t-butylphenol in a 200-milliliter flask fitted with a reflux condenser and a stirrer were added 0.8 g of 6% manganese naphthenate (diluent: terpene) and 1.0 g of 5% copper naphthenate (diluent: terpene) While elevating the temperature, terpene was volatilized. Subsequently, while introducing a dry air at a rate of 140 ml/min, the reaction was run at 170° C for 20 hours.

The composition of the obtained reaction liquid and the reaction selectivity are as follows.

| 2,6-di-t-butylphenol | 23% |
|---|---|
| 3,3',5,5'-tetra-t-butyl-4,4'-dihydroxydiphenyl | 55% |
| 3,3',5,5'-tetra-t-butyl-4,4'-diphenoquinone | 21% |
| asymmetrically dimerized products | 0.0% |
| others | 1% |
| reaction selectivity | 98.7% |

Subsequently, introduction of the dry air was interrupted, and the reaction further continued at 180° C for 10 hours while introducing a nitrogen gas at a rate of 20 ml/min.

At this time, the composition of the reaction liquid is as follows.

| 2,6-di-t-butylphenol | 8% |
|---|---|
| 3,3',5,5'-tetra-t-butyl-4,4'-dihydroxydiphenyl | 84% |
| 3,3',5,5'-tetra-t-butyl-4,4'-diphenoquinone | 5% |
| asymmetrically dimerized products | 0.0% |
| others | 3% |

EXAMPLE 10

The reaction was performed in the same way as in Example 6 and 0.3 g of triethanolamine was then added. While passing nitrogen through the reactor at a rate of 5 ml/min, the reaction was further carried out at 180° C for 30 minutes.

At this time, the composition of the reaction liquid is as follows.

| 3,3'5,5'-tetra-t-butyl-4,4'-diphenoquinone | 41.8% |
|---|---|
| 3,3'5,5'-tetra-t-butyl-4,4'-diphenoquinone | 0.2% |
| 2,6-di-t-butylphenol | 57.1% |
| asymmetrically dimerized products | 0.0% |
| others | 0.9% |

EXAMPLE 11

The reaction was performed in the same way as in Example 1 except using 122 g of 2,6-xylenol instead of 103.3 g of 2,6-di-t-butylphenol and 0.6 g of cobalt naphthenate (5% terpene solution) instead of 1.6 g of manganese naphthenate (8% terpene solution) respectively. The composition of the reaction liquid was analyzed after the oxidation reaction and the disproportionation reaction. The results are as follows.

|  | After oxidation reaction | After disproportionation reaction |
|---|---|---|
| 3,3'5,5'-tetramethyl-4,4'-dihydroxydiphenyl | 6.8% | 13.8% |
| 3,3',5,5'-tetramethyl-4,4'-diphenoquinone | 3.6% | 0.1% |
| 2,6-xylenol | 89.6% | 86.0% |
| asymmetrically dimerized products | 0.0% | 0.0% |
| reaction selectivity | 99.9% | — |

EXAMPLES 12 to 16

The reaction was performed in the same way as in Example 1 except that the starting phenols, the transition metal compound as a catalyst and the deactivator of the catalyst were changed as shown in Table 2. Eight hours after the oxidation reaction and half an hour after the disproportionation reaction, the composition of the reaction liquid was analyzed. The results are shown in Table 2.

TABLE 2

| Example No. | Phenols | Catalyst for oxidation reaction | Catalyst deactivator | Composition of oxidation reaction liquid (after 8 hrs) | | | | | Reaction selectivity |
|---|---|---|---|---|---|---|---|---|---|
|  |  |  |  | Biphenols | Diphenoquinones | Phenols | Asymmetrically dimerized products | Others |  |
| 12 | 2,6-Xylenol 122 g | Manganese naphtenate (5% solution of mineral terpene) 0.7 g Copper naphthenate (5% solution of mineral terpene) 0.2 g | Diethylenetriamine 0.3 g | 29.5% | 8.5% | 61.0% | 0.0% | 1.0% | 97.4% |
| 13 | 2,6-DTBP*2 103 g | Iron naphtenate (5% solution of mineral | Diethanolamine 0.3 g | 38.1% | 13.7% | 47.1% | 0.0% | 1.1% | 97.9% |

TABLE 2-continued

| | | | | Composition of oxidation reaction liquid (after 8 hrs) | | | | | |
|---|---|---|---|---|---|---|---|---|---|
| 14 | 2,6-DTBP*2 103 g | terpene) 2.8 g Manganese naphthenate (5% solution of mineral terpene) 0.4 g Ferric nitrate hexahydrate 0.7 g Manganese nitrate hexahydrate 0.1 g | Ethanolamine 0.2 g | 58.0% | 15.2% | 25.3% | 0.0% | 1.5% | 98.0% |
| 15 | 2,6-Xylenol 122 g | Iron dimethyl-glyoximate 0.6 g | Cysteamine 0.3 g | 10.1% | 13.5% | 74.2% | 0.0% | 2.2% | 91.5% |
| 16 | 2,6-DTBP*2 103 g | Salcomine 0.5 g | Aminophenol 0.5 g | 28.6% | 9.2% | 57.8% | 0.0% | 4.4% | 89.6% |

| | Composition of desproportionation reaction liquid (after 0.5 hr) | | | | |
|---|---|---|---|---|---|
| Example No. | Bi-phenols | Dipheno-quinones | Phenols | Asymmetrically dimerized products | Others |
| 12 | 46.3% | 0.2% | 52.4% | 0.0% | 1.1% |
| 13 | 65.3% | 0.4% | 33.2% | 0.0% | 1.1% |
| 14 | 86.6% | 0.4% | 10.3% | 0.0% | 2.7% |
| 15 | 36.5% | 0.3% | 61.0% | 0.0% | 2.2% |
| 16 | 46.7% | <0.1% | 48.1% | 0.0% | 5.1% |

Note:
*2 2,6-di-t-butylphenol

We claim:

1. A method for symmetrically dimerizing phenols represented by the formula

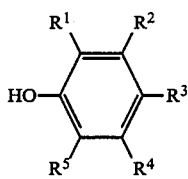

Wherein $R^1$, $R^2$, $R^3$, $R^4$ and $R^5$, which may be the same or different, each denotes a hydrogen atom, a hydrocarbon group having 1 to 8 carbon atoms, an alkoxy group or an allyloxy group, or the adjacent R groups may form a cyclic structure by a bonding group selected from the group consisting of a polymethylene group and a dioxymethylene group, provided at least one of the substituents in the ortho- or para-position is hydrogen, said method comprising
   oxidizing said phenols in molten state in the liquid phase using a metallic soap of a transition metal as a catalyst and an oxygen-containing gas as an oxidizing agent to conduct dimerization.

2. The method of claim 1 wherein the oxidation in the liquid phase is carried out in the substantial absence of a solvent.

3. The method of claim 1 wherein the transition metal compound is a long chain fatty acid salt containing at lesat one metal selected from copper, iron, lead, vanadium, cobalt and manganese.

4. The method of claim 1 wherein the phenols are 2,6-xylenol, 2,3,6-trimethylphenol, 2,6-di-t-butylphenol, o-cresol or 2,4-xylenol.

5. The method of claim 1 wherein said transition metal is present in the form of an ion selected from the group consisting of copper (II), iron (II), iron (III), lead (II), vanadium (V), vanadyl (VO(III)), cobalt (II), manganese (II), manganese (III), molybdenum (V), tungsten (V), palladium (II) and palladium (IV).

6. The method of claim 1, wherein said transition metal is selected from the group consisting of copper, lead, iron, vanadium, cobalt and manganese.

7. The method of claim 1 wherein said transition metal is present in an amount of 0.001 to 2.0 mol % per mol of phenol.

8. The method of claim 1 wherein said oxygen-containing gas is supplied to the reaction so as to supply oxygen at a rate of from 1 ml/min. to 500 ml/min. per mol of phenol.

9. The method of claim 1 wherein said oxidation is carried out at a temperature of 130° to 220° C.

10. A process for producing diphenols which comprises

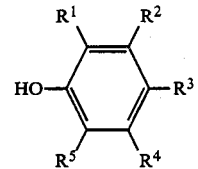

wherein $R^1$, $R^2$, $R^3$, $R^4$ and $R^5$, which may be the same or different, each denotes a hydrogen atom, a hydrocarbon group having 1 to 8 carbon atoms, an alkoxy group or an allyloxy group, or the adjacent R groups may form a cyclic structure by a bonding group selected from the group consisting of a polymethylene group and a dioxymethylene group, provided at least one of the substituents in the ortho- or para-position is hydrogen, in molten state in the liquid phase using a metallic soap of a transition metal as a catalyst and an oxygen-containing gas as an oxidizing agent to conduct dimerization, and
   then interrupting introduction of the oxygen-containing gas to conduct a proton disproportionation reaction.

11. The process of claim 10 wherein the oxidation in the liquid phase is carried out in the substantial absence of a solvent.

12. The process of claim 10 wherein the proton disproportionation reaction is carried out at a temperature higher than the temperature of the oxidation reaction.

13. The process of claim 10 wherein the proton disproportionation reaction is carried out in the presence of a deactivator of the transition metal compound.

14. The process of claim 10 wherein said transition metal is present in the form of an ion selected from the group consisting of copper (II), iron (II), iron (III), lead (II), vanadium (V), vanadyl (VO(III)), cobalt (II), manganese (II), manganese (III), molybdenum (V), tungsten (V), palladium (II) and palladium (IV).

15. The process of claim 10 wherein said transition metal is selected from the group consisting of copper, lead, iron, vanadium, cobalt and manganese.

16. The process of claim 10 wherein said transition metal is present in an amount of 0.01 to 2.0 mol % per mol of phenol.

17. The process of claim 10 wherein said oxygen-containing gas is supplied to the reaction so as to supply oxygen at a rate of from 1 ml/min. to 500 ml/min. per mol of phenol.

18. The process of claim 12 wherein said oxidation is carried out at a temperature of 130° to 220° C.

19. The process of claim 12, wherein said proton disproportionation reaction is carried out at a temperature which is about 10° to 30° C higher than the temperature of said oxidation reaction.

20. The process of claim 13 wherein said deactivator is selected from the group consisting of aminoalcohols, polyamines, polyaminopolyethers, aminothiols, phosphines and aminocarboxylic acids.

* * * * *

UNITED STATES PATENT AND TRADEMARK OFFICE
CERTIFICATE OF CORRECTION

PATENT NO. : 4,962,240

DATED : October 9, 1990

INVENTOR(S) : TAKU KITAMURA, ET AL.

It is certified that error appears in the above-identified patent and that said Letters Patent is hereby corrected as shown below:

Title Page:
    At [73] Assignee: "Danippon Ink and Chemicals, Inc.," should read --Dainippon Ink and Chemicals, Inc.,--.

Signed and Sealed this

Fourth Day of May, 1993

Attest:

MICHAEL K. KIRK

Attesting Officer

Acting Commissioner of Patents and Trademarks